(12) United States Patent
Odierno

(10) Patent No.: US 6,257,408 B1
(45) Date of Patent: Jul. 10, 2001

(54) NEEDLE SHEATHING AND UNSHEATHING SAFETY DEVICE

(76) Inventor: David Odierno, 104 Falcon St., East Boston, MA (US) 02128

( * ) Notice: Subject to any disclaimer, the term of this patent is extended or adjusted under 35 U.S.C. 154(b) by 0 days.

(21) Appl. No.: 09/453,737

(22) Filed: Dec. 2, 1999

(51) Int. Cl.[7] .............................. B65D 83/10; B65D 6/04
(52) U.S. Cl. ........................ 206/366; 206/365; 206/563; 211/85.13
(58) Field of Search ................................. 206/365, 366, 206/562, 563, 370, 571, 364; 211/85.13, 60.1; 604/192, 263

(56) References Cited

U.S. PATENT DOCUMENTS

| | | | |
|---|---|---|---|
| 2,659,485 | * | 11/1953 | Duley et al. .................. 211/85.13 X |
| 3,727,749 | * | 4/1973 | Martin .................. 206/366 |
| 4,383,615 | * | 5/1983 | Aquino .............................. 206/366 X |
| 4,658,957 | * | 4/1987 | Guth et al. ............................ 206/365 |
| 4,753,345 | * | 6/1988 | Goodsir et al. ....................... 206/366 |
| 4,801,012 | * | 1/1989 | Steenhuisen et al. ................ 206/366 |
| 4,836,373 | | 6/1989 | Goldman . |
| 4,844,249 | * | 7/1989 | Coulombe ........................ 206/365 X |
| 4,848,569 | | 7/1989 | Leishman . |
| 4,890,734 | | 1/1990 | Gach . |
| 4,917,243 | | 4/1990 | Abrams et al. . |
| 5,007,535 | * | 4/1991 | Meseke et al. ....................... 206/366 |
| 5,090,564 | * | 2/1992 | Chimienti ............................. 206/365 |
| 5,279,578 | * | 1/1994 | Cooke .................................. 604/192 |
| 5,311,985 | * | 5/1994 | Suida ............................... 206/366 X |
| 5,469,964 | | 11/1995 | Bailey . |
| 5,472,433 | | 12/1995 | Suzuki . |

OTHER PUBLICATIONS

Government Urges Use of Safer Needles, Associated Press Article, usatoday.com, Nov. 22, 1999.

* cited by examiner

Primary Examiner—Bryon P. Gehman

(57) ABSTRACT

A needle sheathing safety device having a plurality of spaced openings for grasping and securely holding a hypodermic needle and cap. This invention features a container body housing; and a plurality of spaced apart and axially aligned openings for grasping and securely holding a needle cap and needle in the body housing. In most embodiments, the body housing is configured to position the user's hands free and clear of the needle during the sheathing and unsheathing operation.

8 Claims, 3 Drawing Sheets

NEEDLE SHEATHING AND UNSHEATHING SAFETY DEVICE

BACKGROUND OF THE INVENTION

This invention relates to medical safety equipment. More particularly, the present invention relates to a safety device for safely sheathing and unsheathing a needle and securely holding a needle.

A major concern for many health care providers is the risk of being exposed to infectious diseases. Of particular concern is the common but potentially life-threatening act of handling hypodermic needles. Health care providers handle hypodermic needles in a variety of settings for a variety of reasons. Included in the uses of hypodermic needles is the administration of medications and the drawing of blood and other bodily fluids. Whenever a used hypodermic needle is handled though, there exists the possibility that the health care provider handling the needle may be accidentally or inadvertently pricked by the now used needle. According to the latest figures available, it is estimated that at least 600,000 health workers accidentally prick themselves each year.

Previously, devices aimed at reducing the potential of inadvertent self-inflicted needle pricks by health care workers proposed have been unduly complicated to manufacture and use. For example, in U.S. Pat. No. 5,469,964, there is disclosed a device that receives the sheath of a needle and engages the sheath by way of rotatable locking means. The device disclosed therein is complex in construction and thus not conducive for use as a disposable device.

SUMMARY OF THE INVENTION

It is therefore an object of this invention to provide a needle sheathing safety device that securely holds the cap of a hypodermic needle, thereby reducing the user's risk of being inadvertently pricked when sheathing and unsheathing the needle.

It is therefore an object of this invention to provide a needle sheathing safety device that securely holds the needle of a hypodermic needle, thereby reducing the user's risk of being inadvertently pricked when sheathing and unsheathing the needle.

It is a further object of the present invention to provide a needle sheathing safety device that is easily manufactured and operated.

It is a further object of the present invention to provide a needle sheathing safety device that retains the needle cap and needle in a secure location for convenient and safe re-sheathing.

This invention results from the realization that an easier to use and therefore safer needle sheathing safety device is effectuated by a needle sheathing safety device having a plurality of spaced openings for grasping and securely holding a hypodermic needle and cap. This invention features a container body housing; and a plurality of spaced apart and axially aligned openings for grasping and securely holding a needle cap and needle in the body housing. In most embodiments, the body housing is configured to position the user's hands free and clear of the needle during the sheathing and unsheathing operation. Additionally, the plurality of axially aligned openings preferably has means for securely retaining the needle cap and needle in the device.

In another embodiment, the needle sheathing safety device has a multiple of plurality of axially aligned openings for accommodating the sheathing, unsheathing and retaining of multiple of needles.

In most embodiments the axially aligned openings are U-shaped to better accept the portion of the hypodermic needle disposed therein. Of course, the openings may take on other shapes as well, such as squared corners. The plurality of axially aligned openings generally comprises an opening located at an end of the body housing and a second of the plurality of openings disposed in the body housing yet in relative close proximity to the opening located in the end of the body housing. The combined configuration of the opening located in the end of the body housing and the second opening positioned next thereto operate to grasp and retain the needle and needle cap in the needle sheathing safety device of the present invention. Other openings which are also axially aligned with the end opening are most often disposed in the body housing for grasping and retaining the needle cap.

This invention is preferably constructed of lightweight, needle puncture-resistant and inexpensive materials such as hard plastics. The important feature of the materials of construction is that the materials prevent the penetration of the needle, thereby alleviating the risks of inadvertent needle pricks. The body housing is generally configured so that the user need not hold the device in the vicinity of the sheathing and unsheathing process. The invention may also be attached to a work surface, thereby obviating the risk that a health care provider prick their free hand with the hypodermic needle.

BRIEF DESCRIPTION OF THE DRAWINGS

Other objects, features and advantages will occur to those skilled in the art from the following description of a preferred embodiment and the accompanying drawings, in which.

DETAILED DESCRIPTION OF THE PREFERRED EMBODIMENT

Figure 1:
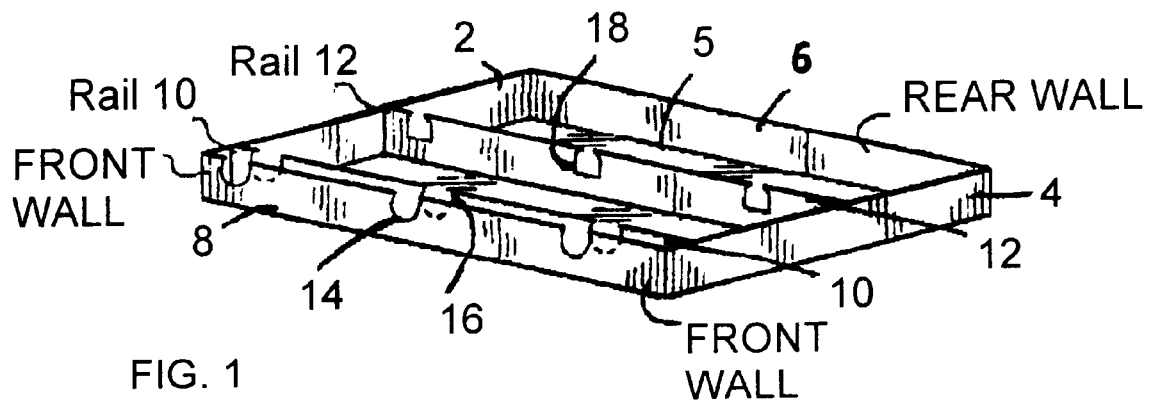
FIG. 1 is a perspective view of the needle sheathing safety device of this invention.

Needle sheathing safety device 1, FIG. 1, of the present invention comprises a body housing comprising a front wall 8, a rear wall 6 and side walls 2 and 4 and a bottom 5. In the preferred embodiment depicted, the body housing is substantially a rectangular-shaped housing containing the other operable structural components of the invention. The front wall 8 has an opening 14, generally U-shaped, to facilitate the placement of a needle hub therein. Accordingly, opening 14 is sized to accept the size of needle hubs that will be used with the needle sheathing safety device 1. Also located in the body housing of the needle sheathing safety device 1 is a rail 10 and a rail 12. Located in the rail 10, are openings 16. Also shown are openings 18 disposed in rail 12.

Figure 6:
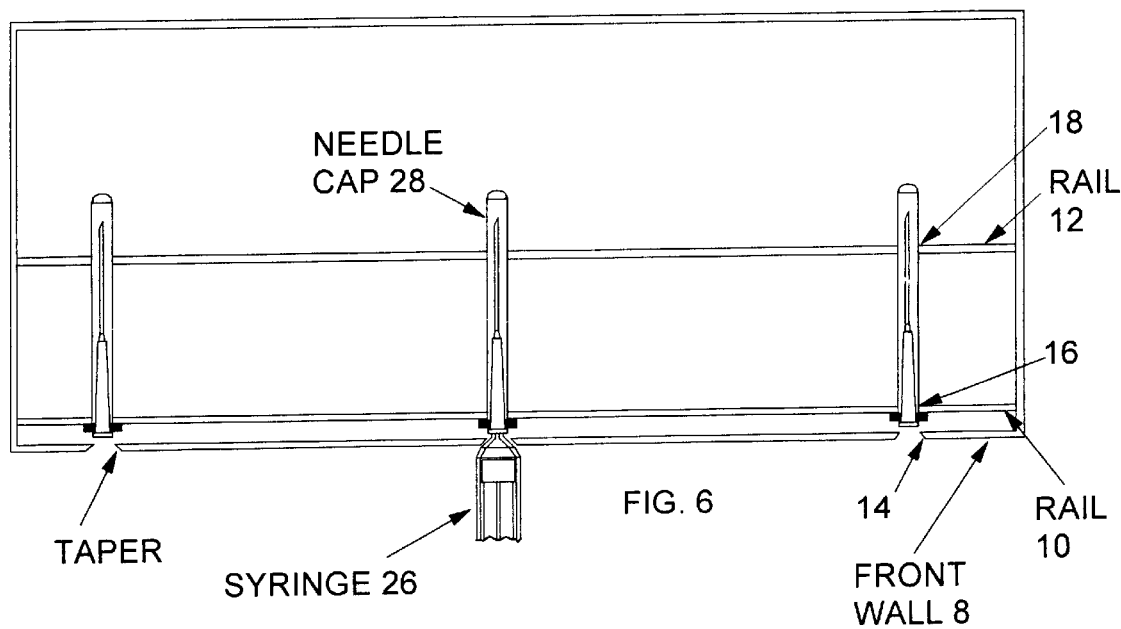
FIG. 6 is a top view of the invention of FIG. 1 depicting three needles and needle caps retained is the invention of FIG. 1.
Figure 7:
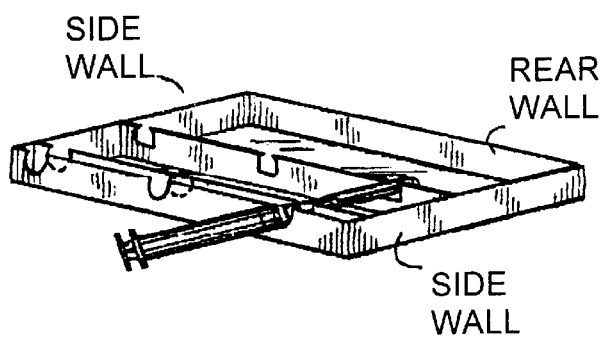
FIG. 7 is perspective view of the present invention of FIG. 1 showing a needle operably positioned therein.

The openings 16 disposed in rail 10 and the openings 18 disposed in rail 12 are each axially aligned with each other and with the openings 14 located in the front wall 8. In other words, for each opening 14 in the front wall 8, there is a corresponding axially aligned opening 16 in rail 10 and a corresponding axially aligned opening 18 in rail 12. The axially aligned openings in the front wall and spaced apart rails 10 and 12 in combination operate to accommodate a needle cap and needle hub during the process of sheathing and unsheathing of a hypodermic needle as shown in FIGS. 6 and 7.

Figure 2:
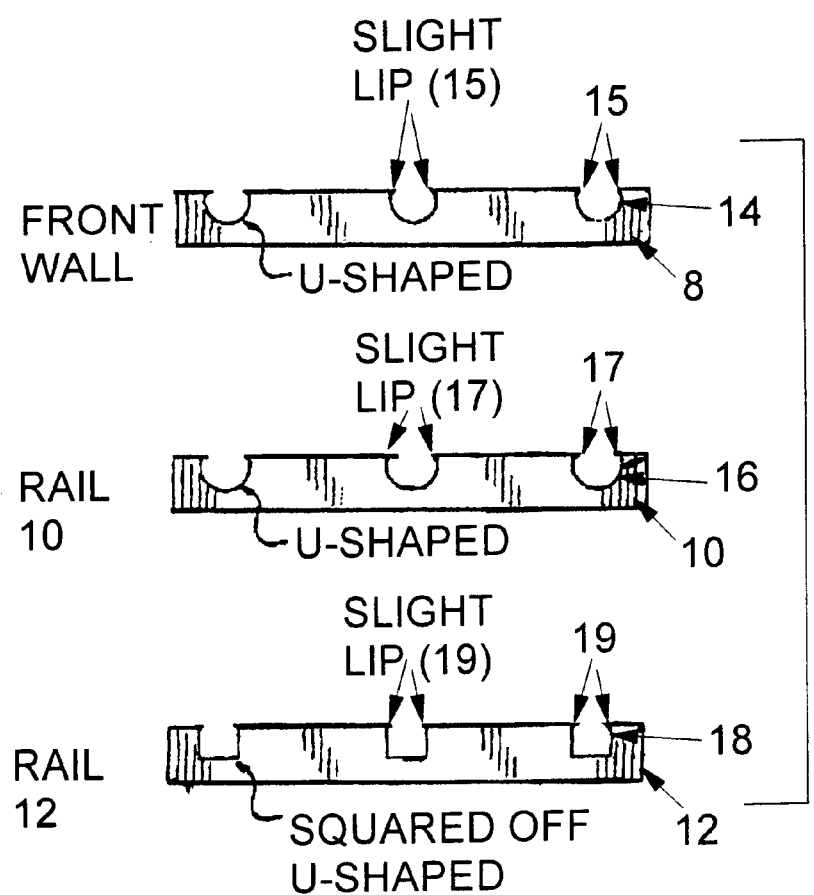
FIG. 2 is a detailed view of the rails comprising the preferred embodiment of the needle sheathing safety device shown in FIG. 1.
Figure 3:
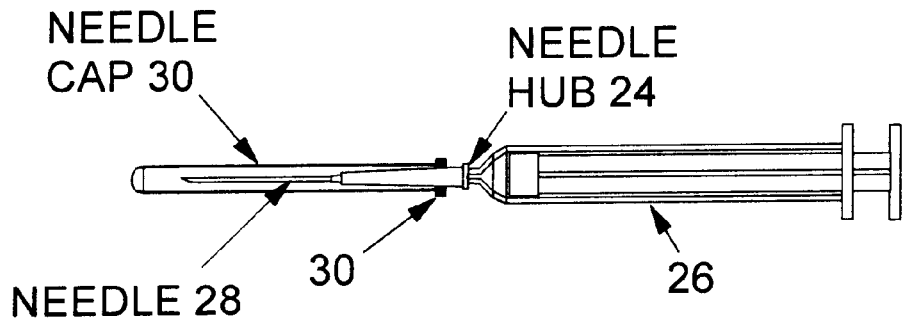
FIG. 3 is a view of a hypodermic needle for use in the invention shown in FIG. 1.

A better understanding of the front wall 8, the rail 10 and the rail 12 may be understood by referring to FIG. 2. The FIG. 2 shows that the front wall 8 and the rail 10 have substantially rounded U-shaped or oval openings, 14 and 16 respectively. Although appearing substantially the same size, the openings 14 in front wall 8 actually extend lower than the rail 10 openings 16. The front wall 8 openings 14 extend lower than the rail 10 openings since the needle hub 24, FIGS. 3 and 4, typically has a greater diameter at the point of contact with the front wall 8 than at the point of contact with rail 10. Although this is the preferred embodiment, the front wall 8 openings and the rail 10 openings may be of the same size. The important feature is that the top of openings 14 and openings 16 extend above the needle hub and needle cap respectively of a hypodermic needle fully and operably inserted into the needle sheathing safety device 1.

Figure 4:
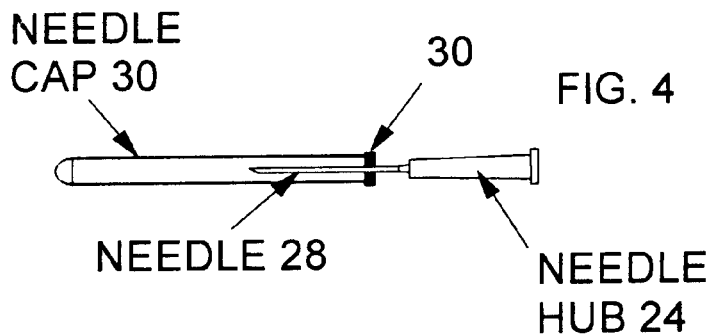
FIG. 4 is a detailed view of the needle hub and cap of the hypodermic needle shown in FIG. 3.

The openings 14, 16 and 18 all have slight "lips" to grasp and securely retain the needle cap and needle in the needle sheathing safety device 1. The FIG. 2 shows the lips on the front wall 8 openings 14 at the upper inside edge of the openings 14; the lips 17 on rail 10 openings 16 at the upper inside edge of the openings 16; and the lips 19 on rail 12 openings 18 at the upper inside edge of openings 18. When the needle cap and needle of a hypodermic needle are inserted into axially aligned openings 14, 16 and 18, the needle cap 20, FIG. 4, is positioned in the opening 18 of rail 12 with the top of the needle cap blow the top of the opening 18. Since the lips 19 extend slightly above and over the top of the seated needle cap 20, the needle cap 20 is held in the opening 18. The fully seated needle cap 20 will also have lips 17 of the opening 16 slightly extending over the rail 10 opening 16. Thus, the needle cap flange 30 is prevented from accidentally becoming disengaged from the opening 16. The fully seated needle cap 20 will also be positioned such that the opening 14 lips 15 extend slightly over the needle hub 24, thereby securely retaining the needle hub 24 in the needle sheathing device 1 until removed by the user.

The front wall 8 and the rail 10 are in relatively close proximity to each other since the needle cap flange 30 is typically relatively thin and the front wall 8 opening 14 grasps the needle hub 30 and the rail 10 opening 16 grasps the needle cap just beyond the needle cap flange 30. In the preferred embodiment, the front wall 8 openings 14 exterior side faces are chamfered, i. e. beveled, so that the needle hub 24 may be easily seated down into the opening 14 and so that the initial unsheathing of the needle cap 20 is done gradually without the need for the user to exert undue force. The beveled exterior face of the openings 14 also eases the re-sheathing process since the syringe 26 may be brought slightly closer to the needle hub 24, close enough to frictionally lock the needle hub 24 onto the needle cap 30 prior to the user lifting and removing the hypodermic needle 100 from the needle sheathing safety device 1. Constructing the body housing of the needle sheathing safety device 1, at least the front wall 8, of resilient materials that give slightly under nominal force from the user also facilitates and eases the re-sheathing process.

Figure 5A:
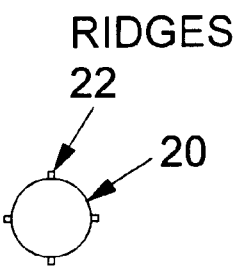
FIG. 5A is a detailed end view of a particular type of needle cap used in the invention of FIG. 1.
Figure 5B:
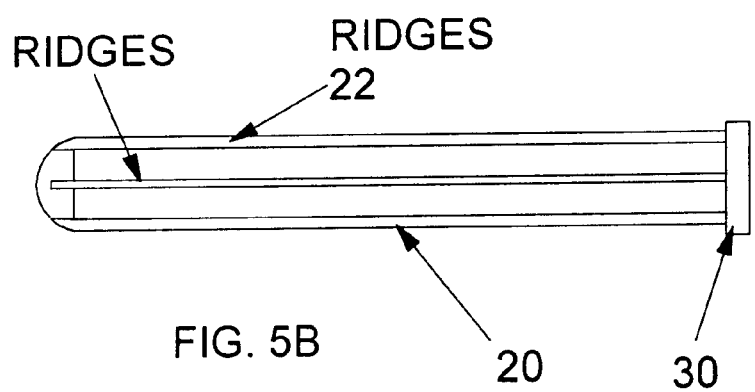
FIG. 5B is a side view of the needle cap of FIG. 5A.

In most embodiments, including the preferred embodiment, the rail 12 openings 18 have squared bottoms. The openings 18 squared-off bottoms are particularly designed to prevent "Leur-Lock" type needle caps, FIG. 5A and 5B, from rotating. This is important when sheathing and unsheathing Leur-Lock needles since these types of needles are threadedly attached to the syringe 26 of the hypodermic needle 100. The squared-off bottoms of openings 18 prevent the needle cap 20 from rotating by impeding the rotation of the needle cap ridges 22 as the syringe 26 is rotated in an effort to remove(or attach) the needle from(to) the syringe 26. Since the needle cap 20 and the needle hub are in frictional contact, the needle 28 is also prevented from rotating. The user may load and unload Leur-Lock needles simply and easily by inserting the needle cap 20 in an opening 18, and then screwing or unscrewing the syringe 26 from the threadedly attached needle hub 24. While the squared-off bottom of opening 18 are particularly useful in the instance of working with threaded-type needles, the squared-off bottoms can adequately accommodate frictionfit needles and needle caps without ridges.

Within the scope of this invention are means for attaching the needle sheathing device 1 of the present invention to a work surface so that the user need not hold the device in their hand. This too reduces the risks of a user becoming accidentally pricked by a contaminated needle. A variety of attachment means are contemplated and covered by this invention as understood by those skilled in the art, including but not limited to adhesive tapes, temporary adhesives, hook and loop fasteners and mechanical means.

Other embodiments will occur to those skilled in the art and are within the following claims:

What I claim is:

1. A needle sheathing safety device for grasping and retaining a needle and needle cap of a hypodermic needle comprising:

a container having a front wall, a rear wall, side walls, and two spaced apart interior walls each parallel with, spaced apart from and about the height of an outside access wall, the outside access wall being one of either the front, rear or side walls, and a bottom wherein the front, rear and side walls are attached to the bottom of said container to form said container having an interior;

at least one axially aligned set of three openings disposed respectively in the outside access wall and the two interior walls; and the openings of a set of openings in the outside access wall and its adjacent interior wall are adapted to be smaller than a flange of the needle cap so that a length of the needle cap may be held in openings of the interior walls and is movable back and forth therein to the extent of the space between the outside access wall and its adjacent interior wall, and the opening in outside access wall is effectively larger than a largest diameter of a needle hub of the needle contained in the needle cap for accepting and retaining the hypodermic needle and needle hub along its longitudinal axis within said axially aligned openings and withdrawal of the needle from the needle cap through the opening in the outside access wall.

2. The needle sheathing safety device of claim 1 further comprising means for retaining the hypodermic needle and needle cap accepted along its longitudinal axis within the axially aligned openings of the needle sheathing safety device.

3. The needle sheathing safety device of claim 2 wherein the means for retaining the hypodermic needle and needle cap are slight lips attached to the upper inside edges of said plurality of openings.

4. The needle sheathing safety device of claim 2 wherein the means for retaining the hypodermic needle and needle cap securely grasps the needle cap and needle hub of the hypodermic needle.

5. The needle sheathing safety device of claim 2 wherein the means for retaining the hypodermic needle and needle cap are slight lips attached to the upper inside edges of said opening disposed in the wall of said needle sheathing safety device.

6. The needle sheathing safety device of claim 1 wherein the openings are substantially U-shaped.

7. The needle sheathing safety device of claim 1 wherein at least one of said plurality of openings is substantially a squared-off U-shaped opening for tending to restrict the rotation of squared-off needle caps that are threadedly attached to and removed from the hypodermic needle.

8. The needle sheathing safety device of claim 1 wherein said container is detachably attached to a work surface, thereby obviating the need for the user to hold the needle sheathing safety device and reducing the risk that a user of the needle sheathing safety device inadvertently prick themselves.

* * * * *